United States Patent [19]
Ehret

[11] Patent Number: 5,849,565
[45] Date of Patent: Dec. 15, 1998

[54] PANIFICATION FERMENT CONTAINING *SACCHAROMYCES CEREVISIAE* STEINERI DSM 9211 AND LACTIC ACID BACTERIA

[75] Inventor: Aloyse Ehret, Blotzheim, France

[73] Assignee: Agrano AG, Allschwil, Switzerland

[21] Appl. No.: 949,198

[22] Filed: Oct. 10, 1997

Related U.S. Application Data

[62] Division of Ser. No. 440,768, May 15, 1995, Pat. No. 5,700,684.

[30] Foreign Application Priority Data

May 27, 1994 [EP] European Pat. Off. ............. 94810306

[51] Int. Cl.⁶ .................. C12N 1/00; C12N 1/20; A01N 63/00
[52] U.S. Cl. .................... 435/252.4; 435/252.9; 435/253.6; 435/255.2; 435/255.21; 435/819; 435/853; 435/855; 435/857; 435/942; 426/62; 424/93.4; 424/93.45; 424/93.51
[58] Field of Search ................. 435/255.2, 255.21, 435/252.4, 252.9, 253.6, 819, 853, 855, 857, 942; 424/93.3, 93.4, 93.45, 93.51; 426/62

[56] References Cited

U.S. PATENT DOCUMENTS

| | | | |
|---|---|---|---|
| 4,745,062 | 5/1988 | Guerineau et al. | 435/209 |
| 4,844,935 | 7/1989 | Fere et al. | 426/549 |
| 4,925,693 | 5/1990 | Lauly | 426/549 |
| 5,200,215 | 4/1993 | Slade et al. | 426/18 |
| 5,211,971 | 5/1993 | VanDijk et al. | 426/18 |
| 5,231,017 | 7/1993 | Lantero et al. | 435/161 |
| 5,283,069 | 2/1994 | VanDijk et al. | 426/18 |
| 5,362,502 | 11/1994 | Slade et al. | 426/20 |
| 5,458,415 | 10/1995 | Poilane | 366/138 |

*Primary Examiner*—David M. Naff
*Assistant Examiner*—Deborah K. Ware
*Attorney, Agent, or Firm*—Tarolli, Sundheim, Covell Tummino & Szabo

[57] ABSTRACT

A biomass constituted of yeast and of lactic acid bacteria, which can be used directly as panification ferment without previous separation of the culture medium and the biomass, is prepared by cocultivating at least one strain of yeast and at least one strain of lactic acid bacteria in a mixed and/or sequential culture, in a culture medium specified in the description. Preferably, the said ferment comprises as yeast the strain *Saccharomyces cerevisiae steineri* DSM 9211 and as lactic acid bacteria one or several strains of *Lactobacillus brevis* DSM 9209, *Lactobacillus plantarum* DSM 9208, *Leuconostoc mesenteroides* DSM 9207 and/or *Pediococcus pentosaceus* DSM 9210.

1 Claim, No Drawings

PANIFICATION FERMENT CONTAINING *SACCHAROMYCES CEREVISIAE* STEINERI DSM 9211 AND LACTIC ACID BACTERIA

This is a divisional of copending application Ser. No. 08/440,768 filed on May 15, 1995, now U.S. Pat. No. 5,700,684.

FIELD OF THE INVENTION

This invention refers to a process for preparing a biomass consisting of yeast and lactic acid bacteria, to the use of the biomass so prepared as panification ferment, as well as to a panification ferment.

BACKGROUND OF THE INVENTION

Actually, there are two main categories of products on the bakery market:

1. The products originating from home bakeries, based on the use of natural sponges of indefinite composition, constituted by undefined microbiological types of eucaryotes and procaryotes, the main representatives of them being microorganisms of the type yeast and/or of the type bacteria. The types mostly used are for the yeasts *Saccharomyces cerevisiae* or Candida, for the bacteria the lactic acid bacteria of the type Lactobacillus. These sponges are mixtures of microorganisms in a unstable equilibrium changing in function of parameters pertaining to the microcosms in which they develop. These uncontrollable parameters, such as the nature of the panification medium (origin of the flour, nature of the flour), or physico-chemical parameters of the production (temperature, climate) influence the reproducibility of the qualities of the final products and inhibit the demand for industrialization of the manufacturing. However, it is true that the sponges lead to products of an appetizing quality which are unanimously acknowledged and sought-after.

2. The standardized products which were obtained under the conditions described in various patents (for example: FR-A-2 525 628 (patent application 82 07047), EP-B1-0 093 635), namely production of selected microorganisms of the type yeasts or bacteria in pure culture. These microorganisms are selected according to their particularites of their metabolism. Often certain types of "improvers" are added to these microorganisms, in order to give quick results, and result in good conservation, aspect and texture of the final products. These products are often added to the traditional baker's yeast, selected and industrially grown on culture mediums based on sugary molasses and chemical additives designed to ameliorate the growth (phosphoric acid, sulfuric acid, ammonia etc.).

This way of action can globally be described as follows: To combine, as powder or paste, cultures of industrial baker's yeast with cultures of selected microorganisms (yeasts and lactic acid bacteria). Chemical additives are added to this mixture. The panification with these "reconstructed" sponges, although it clearly improves the qualities of the final products as compared with industrially obtained panification products with baker's yeast only, is not satisfactory if compared with the home baked products, neither with respect to the organoleptic qualities, nor with respect to the development of the intrinsic quality of the product which contains chemical additives, and as such eliminates the concept of "entirely biological" actually much in demand.

SUMMARY OF THE INVENTION

A first object of the present invention is to eliminate said advantages of the prior art.

Another object of the present invention is to create a biomass consisting of yeast and lactic acid bacteria, based on a cereal medium, the obtained biomass being ready to be used as panification ferment without preliminary separation of the culture medium and the biomass.

The foregoing and other objects, advantages and features of the present invention can be attained by a process wherein at least one strain of yeast and at least one strain of lactic acid bacteria are cocultivated in a mixed culture and/or a sequential culture on a culture medium obtained by a double hydrolysis of a diluted aqueous mixture comprising at least whole-flour and/or wheat germs, namely by the total hydrolysis of the starch into fermentable sugars by the action of at least one alpha-amylase and of at least one amyloglucosidase, and by gentle hydrolysis of at least part of the gluten by proteolytic enzymes of food quality, said culture medium being free of any chemical additives.

The process according to the present invention permits to obtain defined mixtures of identified microorganisms, selected for their metabolical particularities, especially in the metabolism of sugars.

The obtained products are well defined mixtures, allowing—depending on the nature of the selected strains and their representativeness in the mixture—to obtain, in the direct panification of the industrial type, products which are comparable to those obtained with sponges of the traditional type, and this in a perfectly reproducible manner. These mixtures can also be used in the home bakery with the same advantages.

The culture is preferably of the discontinuous alimented type, so called "fed-batch". This technique consists in continuously adding, in repeated periods, the necessary ingredients to a batch of the medium. This type of fermentation allows to control the metabolism of the culture between the aerobic and the anaerobic pathway, thus controlling the metabolic flux between growth (biomass) and the products derived from its metabolism (especially ethanol).

The ethanol content of the culture can be controlled by regulating the alimentation speed to the culture medium, and the partial pressure of the oxygen dissolved in the culture can be controlled by regulating the air supply in accordance with a previously defined slope, maintaining the culture in a metabolism limited in oxygen.

The culture can develop without pH regulation.

Preferably, the coculture is grown as a mixed sequential culture. This means that microorganisms are added deferred in time, permitting to reutilize, at a given time, the products of the metabolism of the microorganisms previously present. Preferably, the culture process is controlled so as to regulate the ethanol content between 0.5 and 10 grams/liter of culture.

Preferably, the process according to the present invention is executed as follows:

a first culture medium (called "base medium") is introduced into a bioreactor;

this first culture medium is inoculated with the yeast and the lactic acid bacteria to be cultivated, distributed in a second culture medium (called "dosage medium");

the bioreactor is continuously fed with the second culture medium;

all this while maintaining a temperature of about 30° C., an aeration controlled by the partial pression of oxygen, and an ethanol concentration of 0.5 to 10 grams/liter of culture.

The obtained product can be used immediately after it left the bioreactor as ferment in the direct industrial panification without any further action, i.e. without previous separation of the culture medium and the biomass. However, generally it is preferable to concentrate the product, either by centrifugation or by filtration, since then the product having a reduced water content can be stored at 3° C. for 21 days without notable diminution of its raising capacity.

Preferably, the used yeast is a strain of *Saccharomyces cerevisiae*, preferably a strain isolated from a natural sponge, and particularly the strain *Saccharomyces cerevisiae steineri* DSM 9211. This strain was isolated from a home made sponge of excellent organoleptic quality. The characteristics of the type *Saccharomyces cerevisiae* are compiled in Table 1.

TABLE 1

Characteristics of *Saccharomyces cerevisiae*

Culture in a liquid medium (dosage medium diluted to one half):
Observation under the microscope: The yeast cells are oval
(2 to 4 × 5 to 7 micrometers) and divide by multipolar budding.
Culture in a solid medium (dosage medium diluted to one half and added by 15 grams/liter of agar-agar):
Observation of the colonies: The yeast colonies are round, smooth, mat, slightly ventricose, and cream-colored.

Metabolism of the sugars:

|  | Assmiliation | Fermentation |
|---|---|---|
| Glucose | + | + |
| L-Arabinose | − | − |
| D-Xylose | − | − |
| Galactose | + | + |
| Cellobiose | − | − |
| Lactose | − | − |
| Maltose | + | + |
| Saccharose | + | + |
| Trehalose | − | − |
| Melezitose | − | − |
| Raffinose | + | − |

The *Saccharomyces cerevisiae steineri* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994, and has been given the accession number DSM 9211.

The complete taxonomic description for the *Saccharomyces cerevisiae steineri* strains is as follows:

Taxonomy of *Saccharomyces cerevisiae steineri* strain DSM 9211
(Morphological and physiological characteristics)

| Yeast Morphology Agar | Form of colony: Smooth, glossy, whole-edge, white |
|---|---|
| Malt Bouillon | Cell form: Oval-Shaped, multipolarly sprouting |
| Cornmeal Agar | No pseudonycellium |
| Malt Agar, V8 Agar | Asci formation: 2 to 4 ascospores per ascus; ascospores being round and smooth, ascus formation directly out from the vegetative cell |

Assimilation and Fermentation
(Percentage of Positively reacting isolates)

| Substrates | Fermentation | Assimilation |
|---|---|---|
| Glucose | 100 | 100 |
| Galactose | 100 | 100 |
| Saccharose | 100 | 100 |
| Maltose | 100 | 100 |
| Lactose | 0 | 0 |
| Raffinose | 0 | 100 |
| Starch | 0 | 0 |
| Melibiose | 0 | 0 |
| Nitrate | 0 | 0 |
| Trehalose | 0 | 0 |
| Cellobiose | 0 | 0 |
| L-Arabinose | 0 | 0 |
| D-Xylose | 0 | 0. |

Preferably, the lactic acid bacteria used are of the type Lactobacillus, Leuconostoc and/or Pediococcus, preferably a strain of *Lactobacillus brevis, Lactobacillus plantarum, Leuconostoc mesenteroides* and/or *Pediococcus pentosaceus*, and in particular one or several of the strains *Lactobacillus brevis* DSM 9209, *Lactobacillus plantarum* DSM 9208, *Leuconostoc mesenteroides* DSM 9207 and *Pediococcus pentosaceus* DSM 9210. These strains were isolated from the same sponge which was the base for the isolation of the above-mentioned strain *Saccharomyces cerevisiae steineri*. The characteristics of these strains are compiled in Table 2.

TABLE 2

Characteristics of the lactic acid bacteria strains

|  | L. plantarum DSM 9208 | L. brevis DSM 9209 | L. mesenteroides DSM 9207 | P. pentosaceus DSM 9210 |
|---|---|---|---|---|
| Control | − | − | − | − |
| Glycerol | − | − | − | − |
| Erythritol | − | − | − | − |
| D-Arabinose | − | − | − | − |
| L-Arabinose | + | + | + | + |
| Ribose | + | + | + | + |
| D-Xylose | − | + | + | − |
| L-Xylose | − | − | − | − |
| Adonitol | − | − | − | − |
| beta-Methyl-xyloside | − | + | − | − |
| Galactose | + | + | + | + |
| D-Glucose | + | + | + | + |
| D-Fructose | + | +/− | + | + |
| D-Mannose | + | − | + | + |
| L-Sorbose | − | − | − | − |
| Rhamnose | +/− | − | − | − |

TABLE 2-continued

Characteristics of the lactic acid bacteria strains

| | L. plantarum DSM 9208 | L. brevis DSM 9209 | L. mesenteroides DSM 9207 | P. pentosaceus DSM 9210 |
|---|---|---|---|---|
| Dulcitol | − | − | − | − |
| Inositol | − | − | − | − |
| Mannitol | + | − | − | − |
| Sorbitol | + | − | − | − |
| alpha-Methyl-D-mannoside | + | − | − | − |
| alpha-Methyl-D-glucoside | + | + | + | − |
| N-Acetyl-glucosamine | + | +/− | + | + |
| Amygdaline | + | − | + | − |
| Arbutine | + | − | + | + |
| Esculine | + | − | + | + |
| Salicine | + | − | + | + |
| Cellobiose | + | − | + | + |
| Maltose | + | + | + | + |
| Lactose | + | − | − | − |
| Melibiose | + | +/− | + | − |
| Saccharose | + | − | + | − |
| Trehalose | + | − | + | − |
| Inuline | − | − | − | − |
| Melezitose | + | − | − | − |
| D-Raffinose | + | − | + | − |
| Starch | − | − | − | − |
| Glycogen | − | − | − | − |
| Xylitol | − | − | − | − |
| beta-Dentibiose | +/− | − | +/− | + |
| D-Turanose | + | − | + | − |
| D-Lyxose | − | − | − | − |
| D-Tagatose | − | − | − | + |
| D-Fucose | − | − | − | − |
| L-Fucose | − | − | − | − |
| D-Arabitol | +/− | − | − | − |
| L-Arabitol | − | − | − | − |
| Gluconate | +/− | +/− | − | − |
| 2-Ceto-gluconate | − | − | − | − |
| 5-Ceto-gluconate | − | +/− | − | − |

The *Leuconostoc mesenteroides* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994, and has been given the accession number DSM 9207.

The complete taxonomic description for the *Leuconostoc mesenteroides* strain is as follows:

Taxonomy of *Leuconostoc mesenteroides* DSM 9207
(Morphological and physiological characteristics)

| Characteristics of colony (2 days, MSR Agar) | Diameter of colony: 0.5 to 1 mm, grey, smooth |
|---|---|
| Cell form and length (MRS Bouillon) | Cocci to short-rod-shaped |
| Lactic acid configuration | D |
| Growth at 15° C. | Reaction positive |
| Growth at 45° C. | Reaction negative |
| End pH in MRS Bouillon | 4.2 |
| Gas formation out of glucose | Reaction positive |
| Ammonia out of arginine | Reaction negative |
| Diamino pimelic acid | Reaction negative |

The *Lactobacillus plantarum* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994, and has been given the accession number DSM 9208.

The complete taxonomic description for the *Lactobacillus plantarum* strain is as follows:

Taxonomy of *Lactobacillus plantarum* DSM 9208
(Morphological and physiological characteristics)

| Characteristics of colony (2 days, MSR Agar) | Diameter of colony: > 1 mm, white, smooth |
|---|---|
| Cell form and length (MRS Bouillon) | Rod-shaped, different lengths, single to chains |
| Lactic acid configuration | DL |
| Growth at 15° C. | Reaction positive |
| Growth at 45° C. | Reaction positive |
| End pH in MRS Bouillon | 3.4 |
| Gas formation out of glucose | Reaction negative |
| Ammonia out of arginine | Reaction negative |
| Diamino pimelic acid | Reaction positive |

The *Lactobacillus brevis* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994, and has been given the accession number DSM 9209.

The complete taxonomic description for the *Lactobacillus brevis* strain is as follows:

Taxonomy of Lactobacillus brevis DSM 9209
(Morphological and physiological characteristics)

| Characteristics of colony (2 days, MSR Agar) | Diameter of colony: > 1 mm, grey, smooth |
|---|---|
| Cell form and length (MRS Bouillon) | Rod-shaped, different lengths, single to chains |
| Lactic acid configuration | DL |
| Growth at 15° C. | Reaction positive |
| Growth at 45° C. | Reaction slightly positive |
| End pH in MRS Bouillon | 4.4 |
| Gas formation out of glucose | Reaction positive |
| Ammonia out of arginine | Reaction positive |
| Diamino pimelic acid | Reaction negative |

The *Pediococcus pentosaceous* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994, and has been given the accession number DSM 9210.

The complete taxonomic description for the *Pediococcus pentosaceous* strain is as follows:

Taxonomy of Pediococcus pentosaceous DSM 9210
(Morphological and physiological characteristics)

| Characteristics of colony (2 days, MSR Agar) | Diameter of colony: > 1 mm, white, smooth |
|---|---|
| Cell form and length (MRS Bouillon) | Cocci, in tetrades, also at pairs |
| Lactic acid configuration | DL |
| Growth at 15° C. | Reaction positive |
| Growth at 45° C. | Reaction positive |
| End pH in MRS Bouillon | 3.7 |
| Gas formation out of glucose | Reaction negative |
| Ammonia out of arginine | Reaction positive |
| Diamino pimelic acid | Reaction negative. |

Preferably, the strain of yeast is grown in a bioreactor in a mixed and/or sequential system in a discontinued alimented culture with one or several lactic acid bacterial strains, depending on the nature of the desired panification product.

The process according to the present invention permits to individually control the metabolism of each microorganism, allowing to act on the concentration of the final metabolites, particularly of the ethanol, the lactic acid and the acetic acid. The choice of the microorganisms on the basis of their metabolic particularities, particularly the homofermentative or heterofermentative metabolic pathway, and notably the regulation of the depending enzymatic activity of pyruvate oxydase oxygen (cf.: Frey, Le Lait 1992) allows to control with great precision the concentration of the acetic acid in the final mixture.

On the other hand, the process according to the present invention allows to defer in time (sequential system) the bringing into action of one microorganism with respect to another.

Several possibilities are feasible:
(1) To simultaneously start a culture of one or several yeasts and of one or several lactic acid bacteria (mixed culture).
(2) To start a culture of one or several yeasts and following it for a determined time, then growing one or several lactic acid bacteria in the culture of yeast, or yeasts, respectively (sequential culture).

The growth of the lactic acid bacteria can start simultaneously (several strains inoculated at the same time) or in a differed way (a first strain put into coculture with the yeast or yeast, respectively, at time $t_1$, then a second strain is introduced at time $t_2 \ldots t_x$).

In the same way, the culture of the lactic acid bacteria can precede the start of the coculture with the yeast or several yeasts.

Table 3 summarizes these possibilities in a simplified schema.

Abbreviation: L.a.b.=Lactic acid bacteria

TABLE 3

Culture Types

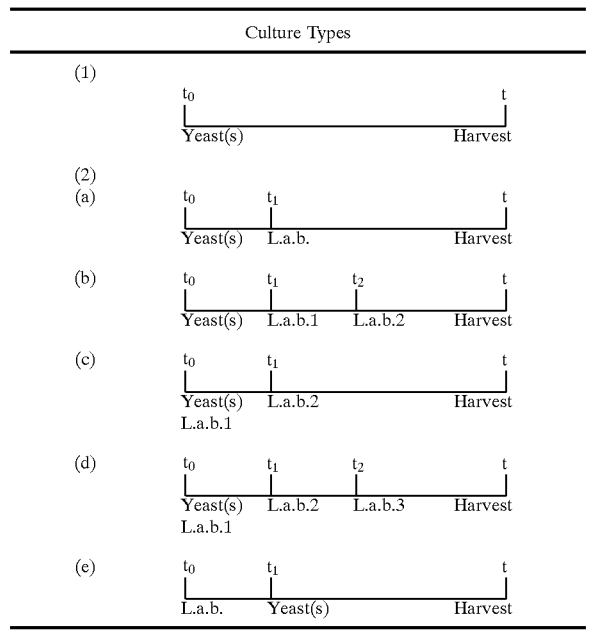

EXAMPLES

A. Ingredients used for the preparation of the culture mediums

The following ingredients are used for the preparation of the culture mediums described hereafter in Examples 1 to 3:

Wheat kernels, ground before use to safeguard the integrity of the nutritional values. A typical analysis of the product is as follows:
water approximately 13%,
total proteins approximately 12%,
carbon hydrates approximately 69%,
total lipids approximately 2%,
starch approximately 59%,
ash 1.5%.

Wheat germs, ground at low speed with controlled reduced heating. A lipid content from 11 to 12% and a starch content of less than 10% should be retained in order to guarantee the quality of the product. A typical analysis of the product is as follows:
water approximately 13%,
total proteins approximately 31.5%,
carbon hydrates approximately 25%,
total lipids approximately 11%,
starch approximately 8%,
ash 5%.

Yeast autolysate of food quality providing the medium with vitamins and amino acids. A typical analysis of the product is as follows:
water approximately 3.5%,
total proteins approximately 50.5%, carbon hydrates approximately 32%,
total lipids approximately 5%,
starch approximately 1.5%,
ash 7.5%.

Sea salt

Industrial water.

B. Preparation of milieu called "dosage medium"

8 liters of water, 1660 grams of ground wheat kernels, 1000 grams of wheat germs, 100 grams of yeast autolysate, 30 grams of sea salt, and 1 milliliters of an alpha-amylase solution (16 unites RAU/gram of starch to be hydrolyzed) are mixed in a bioreactor of 15 liters content.

Thereafter, the mixture is heated to 85° C. for 20 minutes and then cooled to 75° C. Thereafter, 2 milliliters of the same enzyme are added. The temperature is maintained for 20 minutes.

The mixture is cooled to 60° C. Then, 50 milliliters of a solution of amyloglucosidase (16,700 AGI/milliliter) are added. The action of the enzyme is maintained for 90 minutes. The mixture is cooled to 50° C. and subjected to the hydrolysis by two specific proteases, the first one being purified and fractionated papaine, and the second one being fractionated pancreatine.

1.5 milliliters of the first protease per kilogram of flour and 2.3 grams of the second protease per kilogram of flour are used. The action of the proteases lasts 220 minutes.

The obtained culture medium is sterilized at 120° C. for 20 minutes. This medium which is perfectly stable is stored at +4° C.

C. Preparation of the medium called "base medium"

This medium serves for the inoculation and is called in technical terms "tank bottom" in the production system of the biomass according to the process of the discontinued alimented culture ("fed-batch").

10 liters of water, 500 grams of wheat germs, 70 grams of yeast autolysate and 30 grams of sea salt are mixed in a bioreactor.

The medium is subjected to hydrolysis by alpha-amylase (2 milliliters/kilogram of wheat germs) for 20 minutes at 75° C., thereafter to the action of the above-mentioned two specific proteases, i.e. purified and fractionated papaine and fractionated pancreatine, at 50° C. for 240 minutes. The medium is conserved at a +4° C.

The addition of alpha-amylase in two lots to the medium called "dosage medium" avoids the irreversible gelatinisation of the starch at the moment when the temperature raises above 65° C.

D. Analysis of the liberated sugars

For analysis, the liberated sugars are measured by high performance liquid chromatography, and the amino acids liberated by the hydrolysis under the action of the protease are measured by means of the ninhydrine reagent (S. Moore and W. H. Stein, J. Biol. Chem. 176, 367, 1948).

The obtained average values are as follows:

Base medium:
glucose approximately 6 grams/liter,
maltose approximately 12.5 grams/liter,
amino acids approximately 6.5 grams/liter.

Dosage medium:
glucose approximately 86.5 grams/liter,
maltose approximately 11 grams/liter,
amino acids approximately 9 grams/liter.

At no time during the preparation of the medium any chemical additives are involved. The final pH of the medium is near to 6.0, for example 5.5 to 6.5.

E. Culture of microorganisms

This example describes a culture of the type (1) in Table 3.

The microorganisms are kept under conventional conditions in the laboratory and transplanted twice onto the previously defined medium, in order to adapt these microorganisms to the culture medium.

Culture of yeast

The yeast is kept at −80° C. in a cereal medium containing glycerol. It is reisolated on a cereal medium. An isolated colony is put to growth in a liquid cereal medium (dosage medium diluted with one half of water).

A second culture is made from the first one in an Erlenmeyer of 200 milliliters. The cellular density after 16 hours of culture at 30° C. with agitation is $3 \cdot 10^8$ cells/milliliter.

A third culture is made from the second one in 600 milliliters inoculated by 20 milliliters of the previous culture. The cellular density obtained after 8 hours of culture at 30° C. is $2.5 \cdot 10^8$ cells/milliliter. This culture is used to inoculate a 15 liter bioreactor, having an useful capacity 10 liters. The measured ethanol content is 25 grams/liter. The glucose is completely metabolized.

Culture of lactic acid bacteria

The strains, selected for their metabolism and their organoleptic characteristics, are preserved at −80° C. At the time of use, these strains are transplanted onto the solid cereal medium.

Two cultures are made successively in the dosage medium diluted with one half of water.

The first culture is made from a isolated colony put into 100 milliliters of medium. The cellular density attained after 24 hours of culture at 30° C. is 1 to $5 \cdot 10^9$ cells/milliliter, depending on the used type.

The second culture is made in a volume of 900 ml of a new medium inoculated with 100 milliliters of the previous culture. This culture is used for inoculating the bioreactor at the desired time and at the desired concentration.

The particularites of the lactic acid bacteria strains are compiled in Tables 4 to 6.

TABLE 4

| *Lactobacillus plantarum* DSM 9208 | | | | |
|---|---|---|---|---|
| 1st culture: | 1 oese (100 ml of dosage medium diluted to one half) 16 hours - 30° C. - without agitation pH 3.8 - acidity 8.6 - numeration $1.5 \cdot 10^9$ CFU/ml | | | |
| 2nd culture: | dilution of 1st culture to one tenth | | | |
| 2nd culture | | 0 h | 8 h | 16 h | 24 h |
| Numeration [$1 \cdot 10^9$ CFU/ml] | | 0.15 | 1.3 | 2.50 | 3.2 |
| pH | | 5.80 | 4.23 | 3.79 | 3.40 |
| Acidity | | 2.50 | 4.80 | 6.50 | 9.60 |
| Glucose | [g/l] | 25.9 | 20.8 | 28.5 | 16.4 |
| Lactic acid | [g/l] | 0.4 | 3.2 | 5.2 | 8.1 |
| Acetic acid | [g/l] | 0 | 0 | 0 | 0 |
| Ethanol | [g/l] | 0 | 0 | 0 | 0 |

TABLE 5

| *Lactobacillus brevis* DSM 9209 | | | | |
|---|---|---|---|---|
| 1st culture: | 1 oese (100 ml of dosage medium diluted to one half) 16 hours - 30° C. - without agitation pH 4.46 - acidity 7.8 - numeration $3.8 \cdot 10^9$ CFU/ml | | | |
| 2nd culture: | dilution of the 1st culture to one tenth | | | |
| 2nd culture | | 0 h | 8 h | 16 h | 24 h |
| Numeration [$1 \cdot 10^9$ CFU/ml] | | 0.30 | 1.2 | 2.0 | 3.2 |
| pH | | 5.99 | 5.07 | 4.75 | 4.45 |
| Acidity | | 2.0 | 2.8 | 3.5 | 4.0 |
| Glucose | [g/l] | 27.2 | 25.3 | 24.1 | 22.7 |
| Lactic acid | [g/l] | 0.40 | 0.84 | 1.15 | 1.65 |
| Acetic acid | [g/l] | 0.20 | 0.42 | 0.50 | 0.80 |
| Ethanol | [g/l] | 0.10 | 0.17 | 0.25 | 0.50 |

TABLE 6

Leuconostoc mesenteroides DSM 9207

| 1st culture: | 1 oese (100 ml dosage medium diluted to one half) 16 hours - 30° C. |
|---|---|
| 2nd culture: | dilution of the 1st to one tenth 24 hours - 30° C. - without agitation |

| 2nd culture | | 24 h |
|---|---|---|
| Numeration [1 · 10⁹ CFU/ml] | | 1.8 |
| pH | | 3.85 |
| Acidity | | 9.6 |
| Glucose | [g/l] | 28.3 |
| Lactic acid | [g/l] | 3.02 |
| Acetic acid | [g/l] | 0.57 |
| Ethanol | [g/l] | 0.89 |

TABLE 7

Pediococcus pentosaceus DSM 9210

| 1st culture: | 1 oese (100 ml dosage medium diluted to one half) 16 hours - 30° C. |
|---|---|
| 2nd culture: | dilution of the 1st to one tenth 24 hours - 30° C. - without agitation |

| 2nd culture | | 24 h |
|---|---|---|
| Numeration [1 · 10⁹ CFU/ml] | | 2.3 |
| pH | | 3.42 |
| Acidity | | 11.6 |
| Glucose | [g/l] | 15.6 |
| Lactic acid | [g/l] | 9.5 |
| Acetic acid | [g/l] | 0 |
| Ethanol | [g/l] | 0 |

F. Start of the mixed or sequential culture

The ultimate aim, which conditions the start of the process according to the present invention, is to obtain a preparation composed by a mixed culture allowing the preparation of a bread comparable to a bread made with a traditional sponge. The mixed microbial growth brings about numerous interactions of the type commensalism, mutualism and ammensalism between the strains involved. The process described hereafter tries to make a compromise in producing Lactobacillus in sufficient quantity to produce flavors and a characteristic acidity to the breads, and to secure a sufficient proportion of yeasts (rising agents) which guarantee a well aerated bread with good density without further addition of yeast.

Example 1

The culture starts with the growth of yeast. 5 liters of base medium and 600 milliliters of a yeast culture in an Erlenmeyer are continuously introduced into a 15 liter bioreactor, having a useful capacity of 10 liter. The mixture is fed with the dosage medium, and the temperature is maintained at 30° C. The pH, which is continuously measured, is not regulated. At the start the pH is 6, and it goes to 4.0 to 5.0 at the end of the mixed culture, depending on the strain of lactic acid bacteria used. The ethanol content is maintained between 0.5 and 10 grams/liter, by submission of the alimentation of the dosage medium. The agitation is effected by means of two agitator blades of the Rushton type (Size of the blades: one third of the diameter of the bioreactor—Transfer coefficient: 600 mmoles $O_2$/liter—Agitation speed: 500 to 1,200 rpm—Exit of sterile air: varying from 0 to 30 liters/minute). Said air exit depends on the partial pressure of oxygen which is continuously measured by means of a $pO_2$ electrode (Ingold), and is kept above 10%.

The delayed inoculation of lactic acid bacteria allows to adjust the concentrations of various microorganisms and to influence thereupon the organoleptic qualities of the final product.

Table 8 shows a sequential culture in which *Lactobacillus plantarum* is added to the yeast culture 8 hours after its inoculation.

Example 2

This example (cf. Table 9) shows a coculture which consists, at the start, in a mixed culture of yeast and *Leuconostoc mesenteroides*. This mixed culture is followed for 8 hours. After these 8 hours a pre-culture of *Lactobacillus plantarum* is added. The final product is obtained after 18 hours.

Example 3

This example (cf. Table 10) shows a coculture of the same type as that of Example 2, but in this test *Leuconostoc mesenteroides* is replaced by *Lactobacillus brevis* in the coculture at the start. *Lactobacillus plantarum* is added after 8 hours.

It is interesting to note the increase in production of lactic acid as compared with Example 2 (2.40 grams/liter against 1.81 grams/liter).

It is also interesting to note that in the case of the coculture part of the final metabolites produced by one of the microbial types is reutilized by the other types, thus influencing the final organoleptic qualities (reutilized lactic acid and acetic acid).

Depending on the test (cf. Tables 11 to 4), the obtained cellular density ratios between yeasts and bacteria are 3 to 5 ($10^9$ yeasts to 3 to 5·$10^9$ bacteria).

The final culture is cooled to 3° C. as quickly as possible. It can be stored for 8 days without loosing its panification capacity. It is used in a concentration of 20% (weight/volume).

The taste of the "sour dough" of the breads is excellent.

TABLE 8

Mixed sequential culture in the bioreactor
A culture of *Lactobacillus plantarum* is added after 8 hours to a pure yeast culture

| | | Air | | | | | | Numeration x $10^8$ CFU/ml | |
|---|---|---|---|---|---|---|---|---|---|
| Hours | Temperature °C. | Agitation rpm | flow l/min | $pO_2$ % | pH | Ethanol g/l | Dosage % | Yeast | *L. plantarum* |
| 0 | 30 | 500 | 15 | 80.7 | 6.00 | 2.01 | 0 | 0.25 | |
| 4 | 30 | 500 | 15 | 71.1 | 5.60 | 3.47 | 5 | 1.05 | |
| 8 | 30 | 500 | 15 | 38.9 | 4.55 | 4.01 | 10 | 4.0 | 1.0 |

TABLE 8-continued

Mixed sequential culture in the bioreactor
A culture of *Lactobacillus plantarum* is added after 8 hours to a pure yeast culture

| | | Air | | | | | Dosage | Numeration x 10$^8$ CFU/ml | |
|---|---|---|---|---|---|---|---|---|---|
| Hours | Temperature °C. | Agitation rpm | flow 1/min | pO$_2$ % | pH | Ethanol g/l | % | Yeast | *L. plantarum* |
| 12 | 30 | 900 | 21 | 41.2 | 4.29 | 3.11 | 40 | 10.0 | 2.0 |
| 16 | 30 | 1200 | 27 | 43.5 | 4.19 | 3.01 | 100 | 18.0 | 4.5 |

TABLE 9

Mixed culture from start in the bioreactor
A culture of homofermentative bacteria (yeast + *Leuconostoc mesenteroides* + *Lactobacillus plantarum*) is added after 8 hours to culture of yeast + heterofermentative bacteria

| | | Air | | | | | Lactic | Acetic | | Numeration x 10$^8$ CFU/ml | | |
|---|---|---|---|---|---|---|---|---|---|---|---|---|
| Hours | Temperature °C. | Agitation rpm | flow 1/min | pO$_2$ % | pH | Ethanol g/l | acid g/l | acid g/l | Dosage % | Yeast | Hetero- ferment. | Homo- ferment. |
| 0 | 30 | 500 | 15 | 78.1 | 4.52 | 2.48 | 0.72 | 0.22 | 0 | 0.25 | 4.0 | 0 |
| 8 | 30 | 500 | 15 | 27.4 | 4.30 | 2.46 | 1.04 | 0.35 | 10 | 3.0 | 30.0 | 5.0 |
| 12 | 30 | 600 | 18 | 28.9 | 4.29 | 3.67 | 1.68 | 0.48 | 30 | 5.4 | 36.0 | 8.0 |
| 18 | 30 | 700 | 21 | 13.2 | 4.30 | 9.11 | 1.81 | 0.63 | 100 | 10.0 | 40.0 | 10.0 |

TABLE 10

Mixed culture from start in the bioreactor
A culture of homofermentative bacteria (yeast + *Lactobacillus brevis* + *Lactobacillus plantarum*) is added after 8 hours to a culture of yeast + heterofermentative bacteria

| | | Air | | | | | Lactic | Acetic | | Numeration x 10$^8$ CFU/ml | | |
|---|---|---|---|---|---|---|---|---|---|---|---|---|
| Hours | Temperature °C. | Agitation rpm | flow 1/min | pO$_2$ % | pH | Ethanol g/l | acid g/l | acid g/l | Dosage % | Yeast | Hetero- ferment. | Homo- ferment. |
| 0 | 30 | 500 | 15 | 79.2 | 4.40 | 2.54 | 0.89 | 0.33 | 0 | 0.28 | 6.0 | 0 |
| 8 | 30 | 500 | 15 | 42.4 | 4.21 | 2.86 | 1.12 | 0.35 | 10 | 2.7 | 10.0 | 5.0 |
| 12 | 30 | 600 | 18 | 42.3 | 4.18 | 3.89 | 1.64 | 0.42 | 35 | 5.5 | 15.0 | 10.0 |
| 18 | 30 | 700 | 21 | 18.4 | 4.31 | 10.21 | 2.49 | 0.56 | 100 | 10.0 | 20.0 | 15.0 |

TABLE 11

Mixed culture from start in the bioreactor
Culture of yeast + heterofermentative bacteria + homofermentative bacteria
(yeast + *Lactobacillus brevis* (12,5 ml) + *Lactobacillus plantarum* (12,5 ml).

| | | Air | | | | | Lactic | Acetic | | Numeration x 10$^8$ CFU/ml | | |
|---|---|---|---|---|---|---|---|---|---|---|---|---|
| Hours | Temperature °C. | Agitation rpm | flow 1/min | pO$_2$ % | pH | Ethanol g/l | acid g/l | acid g/l | Dosage % | Yeast | Hetero- ferment. | Homo- ferment. |
| 0 | 30 | 500 | 15 | 82.8 | 5.45 | 1.87 | 0 | 0.58 | 0 | 0.25 | 0.05 | 0.025 |
| 8 | 30 | 500 | 15 | 34.0 | 4.67 | 4.37 | 0 | 0.50 | 11 | 3.5 | 3.5 | 1.5 |
| 12 | 30 | 700 | 21 | 42.1 | 4.32 | 3.15 | 0.81 | 0.71 | 40 | 9.0 | 10.0 | 5.0 |
| 18 | 30 | 1100 | 27 | 41.3 | 4.23 | 3.04 | 1.10 | 0.95 | 100 | 20.0 | 20.0 | 10.0 |

TABLE 12

Mixed culture from start in the bioreactor
Culture of yeast + heterofermentative bacteria + homofermentative bacteria
(yeast + *Lactobacillus brevis* (25 ml) + *Lactobacillus plantarum* (25 ml).

| | | Air | | | | | Lactic | Acetic | | Numeration × $10^8$ CFU/ml | | |
|---|---|---|---|---|---|---|---|---|---|---|---|---|
| Hours | Temperature °C. | Agitation rpm | flow 1/min | $pO_2$ % | pH | Ethanol g/l | acid g/l | acid g/l | Dosage % | Yeast | Hetero- ferment. | Homo- ferment. |
| 0 | 30 | 500 | 15 | 76.8 | 5.35 | 2.33 | 0 | 0.63 | 0 | 0.24 | 0.10 | 0.05 |
| 8 | 30 | 500 | 15 | 20.2 | 4.69 | 3.88 | 0 | 0.88 | 11 | 3.85 | 5.0 | 3.0 |
| 12 | 30 | 900 | 21 | 29.9 | 4.23 | 3.13 | 1.01 | 0.67 | 34 | 10.0 | 10.0 | 6.0 |
| 18 | 30 | 1100 | 27 | 30.1 | 4.13 | 2.44 | 1.97 | 1.00 | 100 | 20.0 | 22.0 | 12.0 |

TABLE 13

Mixed culture from start in the bioreactor
Culture of yeast + heterofermentative bacteria + homofermentative bacteria
(yeast + *Lactobacillus brevis* (50 ml) + *Lactobacillus plantarum* (50 ml).

| | | Air | | | | | Lactic | Acetic | | Numeration × $10^8$ CFU/ml | | |
|---|---|---|---|---|---|---|---|---|---|---|---|---|
| Hours | Temperature °C. | Agitation rpm | flow 1/min | $pO_2$ % | pH | Ethanol g/l | acid g/l | acid g/l | Dosage % | Yeast | Hetero- ferment. | Homo- ferment. |
| 0 | 30 | 500 | 15 | 77.2 | 5.30 | 1.86 | 0 | 0.59 | 0 | 0.25 | 0.19 | 0.11 |
| 8 | 30 | 500 | 15 | 31.8 | 4.61 | 4.21 | 0 | 0.65 | 10.5 | 4.0 | 8.0 | 8.0 |
| 12 | 30 | 900 | 21 | 36.5 | 4.11 | 3.26 | 1.83 | 0.86 | 41 | 9.5 | 16.0 | 16.0 |
| 16 | 30 | 1100 | 27 | 45.2 | 4.05 | 2.81 | 1.97 | 0.91 | 100 | 19.0 | 30.0 | 30.0 |

TABLE 14

Mixed culture from start in the bioreactor
Culture of yeast + heterofermentative bacteria + homofermentative bacteria
(yeast + *Lactobacillus brevis* (200 ml) + *Lactobacillus plantarum* (200 ml).

| | | Air | | | | | Lactic | Acetic | | Numeration × $10^8$ CFU/ml | | |
|---|---|---|---|---|---|---|---|---|---|---|---|---|
| Hours | Temperature °C. | Agitation rpm | flow 1/min | $pO_2$ % | pH | Ethanol g/l | acid g/l | acid g/l | Dosage % | Yeast | Hetero- ferment. | Homo- ferment. |
| 0 | 30 | 500 | 15 | 81.2 | 4.94 | 1.79 | 0.7 | 0.54 | 0 | 0.25 | 1.0 | 0.6 |
| 8 | 30 | 500 | 15 | 37.3 | 4.69 | 4.64 | 0.5 | 1.25 | 10 | 4.0 | 12.0 | 10.0 |
| 12 | 30 | 900 | 21 | 36.6 | 4.02 | 3.67 | 2.9 | 0.80 | 43 | 10.0 | 25.0 | 25.0 |
| 16 | 30 | 1100 | 27 | 41.8 | 4.08 | 4.48 | 3.7 | 0.83 | 100 | 19.0 | 40.0 | 50.0 |

What is claimed is:

1. A panification ferment comprising *Saccharomyces cerevisiae steineri* DSM 9211 and at least one lactic acid bacteria selected from the group consisting of *Lactobacillus brevis* DSM 9209, *Lactobacillus antarum* DSM 9208, *Leuconostoc mesenteroides* DSM 9207 and *Pediococcus pentosaceus* DSM 9210.

UNITED STATES PATENT AND TRADEMARK OFFICE
CERTIFICATE OF CORRECTION

PATENT NO. : 5,849,565
DATED : December 15, 1998
INVENTOR(S) : Aloyse Ehret

It is certified that error appears in the above-identified patent and that said Letters Patent is hereby corrected as shown below:

Col. 15, line 52
  replace "antarum"
  with --plantarum--.

Signed and Sealed this

Eighth Day of June, 1999

Attest:

Q. TODD DICKINSON

*Attesting Officer*    *Acting Commissioner of Patents and Trademarks*